(12) United States Patent
Uchimura

(10) Patent No.: US 11,202,845 B2
(45) Date of Patent: Dec. 21, 2021

(54) AIR PURIFIER

(71) Applicant: SHARP KABUSHIKI KAISHA, Sakai (JP)

(72) Inventor: Kensuke Uchimura, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 173 days.

(21) Appl. No.: 16/498,314

(22) PCT Filed: Aug. 22, 2017

(86) PCT No.: PCT/JP2017/029861
§ 371 (c)(1),
(2) Date: Sep. 26, 2019

(87) PCT Pub. No.: WO2018/189924
PCT Pub. Date: Oct. 18, 2018

(65) Prior Publication Data
US 2020/0030478 A1 Jan. 30, 2020

(30) Foreign Application Priority Data
Apr. 10, 2017 (JP) .............................. JP2017-077725

(51) Int. Cl.
| | |
|---|---|
| *A61L 9/014* | (2006.01) |
| *F24F 7/00* | (2021.01) |
| *F24F 11/50* | (2018.01) |
| *F24F 11/52* | (2018.01) |
| *F24F 8/108* | (2021.01) |

(Continued)

(52) U.S. Cl.
CPC .............. *A61L 9/014* (2013.01); *F24F 7/00* (2013.01); *F24F 8/108* (2021.01); *F24F 8/30* (2021.01); *F24F 11/50* (2018.01); *F24F 11/52* (2018.01); *A61L 2209/111* (2013.01);
(Continued)

(58) Field of Classification Search
None
See application file for complete search history.

(56) References Cited

FOREIGN PATENT DOCUMENTS

| | | |
|---|---|---|
| CN | 202837895 U | 3/2013 |
| CN | 202973370 U | 6/2013 |

(Continued)

OTHER PUBLICATIONS

Koseto, J. JP2015090251A—translated document (Year: 2015).*
(Continued)

*Primary Examiner* — Jelitza M Perez
(74) *Attorney, Agent, or Firm* — ScienBiziP, P.C.

(57) ABSTRACT

An air purifier performing an air purifying operation by drive of an air blower, and the air purifier includes: a housing in which an inlet and outlets and are opened; an air passage that connects the inlet and the outlets and; the air blower that is disposed in the air passage; a pre-filter that is disposed so as to face the inlet; and an operation panel that has a plurality of touch keys to and a plurality of light sources which correspond to the respective touch keys, in which a human body detection unit that detects presence/absence of a person is provided in the housing, and an LED of a predetermined touch key of a first group is turned off when a person is not detected by the human body detection unit, and is turned on or blinks when a person is detected by the human body detection unit.

12 Claims, 9 Drawing Sheets

(51) Int. Cl.
 *F24F 8/30* (2021.01)
 *F24F 120/10* (2018.01)
(52) U.S. Cl.
 CPC ....... *A61L 2209/12* (2013.01); *A61L 2209/14* (2013.01); *F24F 2120/10* (2018.01)

(56) References Cited

FOREIGN PATENT DOCUMENTS

| | | | |
|---|---|---|---|
| CN | 204678540 U | | 9/2015 |
| CN | 105371377 A | | 3/2016 |
| CN | 106292323 A | | 1/2017 |
| CN | 106440090 A | | 2/2017 |
| JP | 2017-058041 A | | 3/2007 |
| JP | 2009-192132 A | | 8/2009 |
| JP | 2009192132 A | * | 8/2009 |
| JP | 2009274050 A | | 11/2009 |
| JP | 2015-090251 A | | 5/2015 |
| JP | 2015090251 A | * | 5/2015 |
| JP | 2016050687 A | * | 4/2016 |
| TW | 461953 B | | 11/2001 |
| TW | M473493 U | | 3/2014 |
| TW | M530928 U | | 10/2016 |

OTHER PUBLICATIONS

Yumiba, D. JP2009192132A—translated document (Year: 2009).*
Hiruta, Y. JP2016050687A—translated document (Year: 2016).*
English translation of the Official Action dated Jul. 23, 2018 in the corresponding Taiwan patent application No. 106129685.

* cited by examiner

AIR PURIFIER

TECHNICAL FIELD

The disclosure relates to an air purifier that includes a touch key.

BACKGROUND ART

PTL 1 discloses a air purifier in the related art. The air purifier has a housing in which an inlet and an outlet are opened. In an upper part of the housing, an operation panel in which touch keys of an electrostatic capacitance type are disposed is provided. An air passage that connects the inlet and the outlet is provided in the housing, and an air blower is disposed in the air passage. A filter is disposed so as to face the inlet.

In the air purifier that has the aforementioned configuration, when an operation is started, the air blower is driven and air in a living room is sucked from the inlet. The air sucked from the inlet is sent out from the outlet after dust is collected by the filter. It is thereby possible to perform air purification in the living room.

CITATION LIST

Patent Literature

PTL 1: Japanese Unexamined Patent Application Publication No. 2017-58041 (Pages 5 to 9, FIG. 2)

SUMMARY

Technical Problem

An operation panel that has touch keys of an electrostatic capacitance type generally includes a plurality of light sources that corresponds to the respective touch keys, and a sheet in which a character or the like is provided so that light is able to be transmitted therethrough is disposed between the touch keys and the light sources. The touch keys are displayed so as to be visually recognizable when the light sources are turned on, so that a user is able to recognize a desired touch key on the operation panel to perform an operation input.

However, according to the aforementioned air purifier in the related art, light sources of the touch keys are always turned on, so that there is a problem that power consumption of the air purifier is increased.

An object of the disclosure is to provide an air purifier capable of reducing power consumption.

Solution to Problem

In order to achieve the aforementioned object, the disclosure provides an air purifier performing an air purifying operation by drive of an air blower, and the air purifier includes: a housing in which an inlet and an outlet are opened; an air passage that connects the inlet and the outlet; the air blower that is disposed in the air passage; a filter that is disposed so as to face the inlet; and an operation panel that has a plurality of touch keys and a plurality of light sources which correspond to the respective touch keys, in which a human body detection unit that detects presence/absence of a person is provided in the housing, and a light source of a predetermined touch key of a first group is turned off when a person is not detected by the human body detection unit, and is turned on or blinks when a person is detected by the human body detection unit.

Moreover, in the disclosure, it is preferable that the air purifier having the aforementioned configuration includes a communication unit that performs wireless communication, in which the light source of the touch key of a second group that is different from the first group is always turned on, and the touch key of the second group includes a communication key by which whether or not communication by the communication unit is allowed is instructed.

Moreover, in the disclosure, it is preferable that, in the air purifier having the aforementioned configuration, the light source of the touch key of a second group that is different from the first group is always turned on, and the touch key of the second group includes a start key by which start or stop of the air purifying operation is instructed.

Moreover, in the disclosure, it is preferable that, in the air purifier having the aforementioned configuration, a light amount of the light source is increased when the touch key the light source of which is turned on is operated.

Moreover, in the disclosure, it is preferable that, in the air purifier having the aforementioned configuration, the predetermined touch key is assigned a function for long press, which is different from that for short press, and the light source is caused to blink at a time of the long press.

Moreover, in the disclosure, it is preferable that the air purifier having the aforementioned configuration includes the touch key of a third group, the light source of which is turned on when the touch key of the first group is operated.

Moreover, in the disclosure, it is preferable that, in the air purifier having the aforementioned configuration, the operation panel has a notification unit that is displayed when a light source for display is turned on, and the light source for display is turned off when a person is not detected by the human body detection unit, and is turned on or blinks when a person is detected by the human body detection unit.

Advantageous Effects of Disclosure

According to the disclosure, a human body detection unit that detects presence/absence of a person is provided in a housing of an air purifier, and a light source of a predetermined touch key of a first group is turned off when a person is not detected by the human body detection unit, and is turned on or blinks when a person is detected by the human body detection unit. Thereby, in a case where a person is not detected by the human body detection unit, the light source of the touch key of the first group is turned off, thus making it possible to reduce power consumption of the air purifier.

DESCRIPTION OF EMBODIMENTS

First Embodiment

Figure 1:
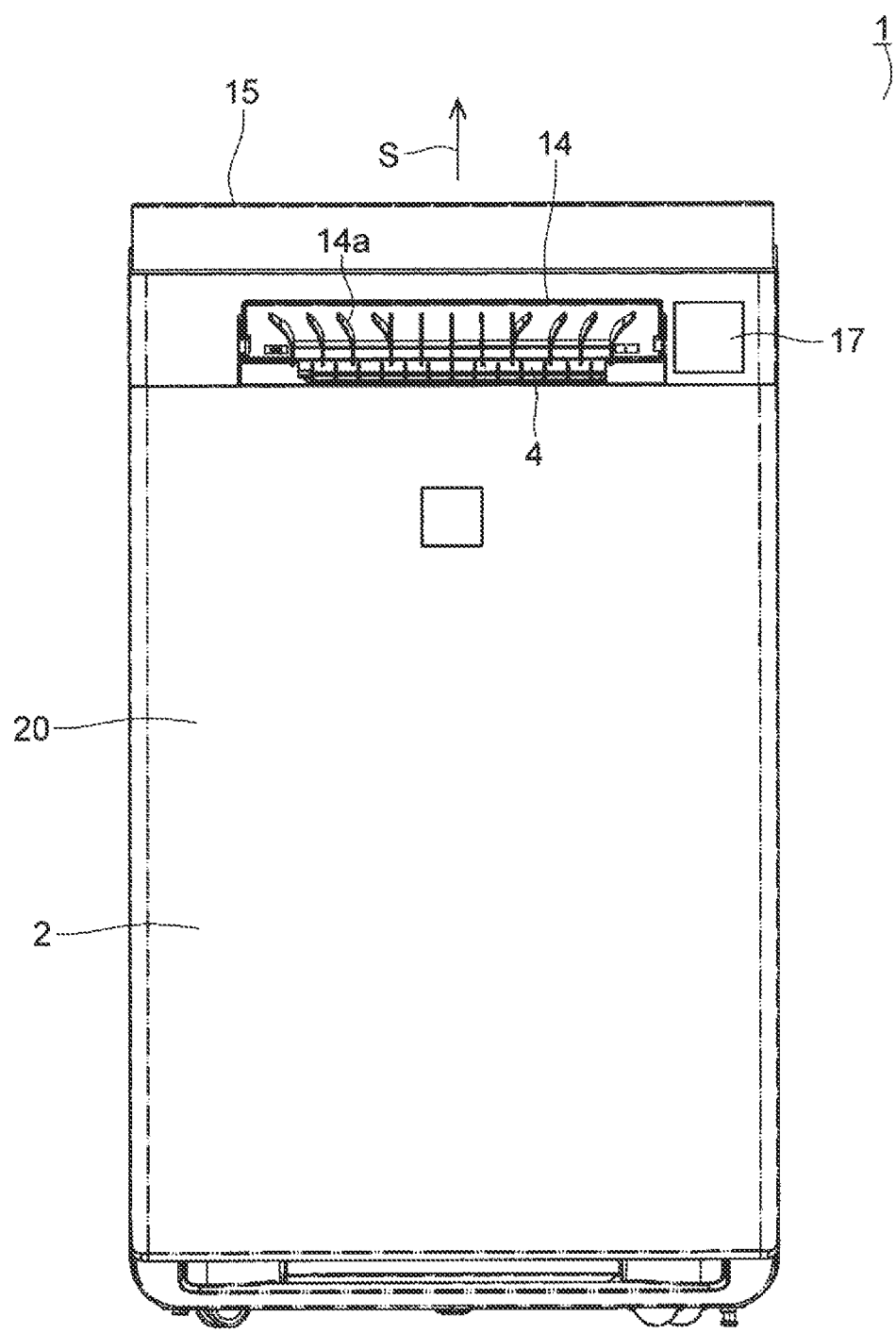
FIG. 1 is a front view illustrating an air purifier of a first embodiment of the disclosure.
Figure 2:
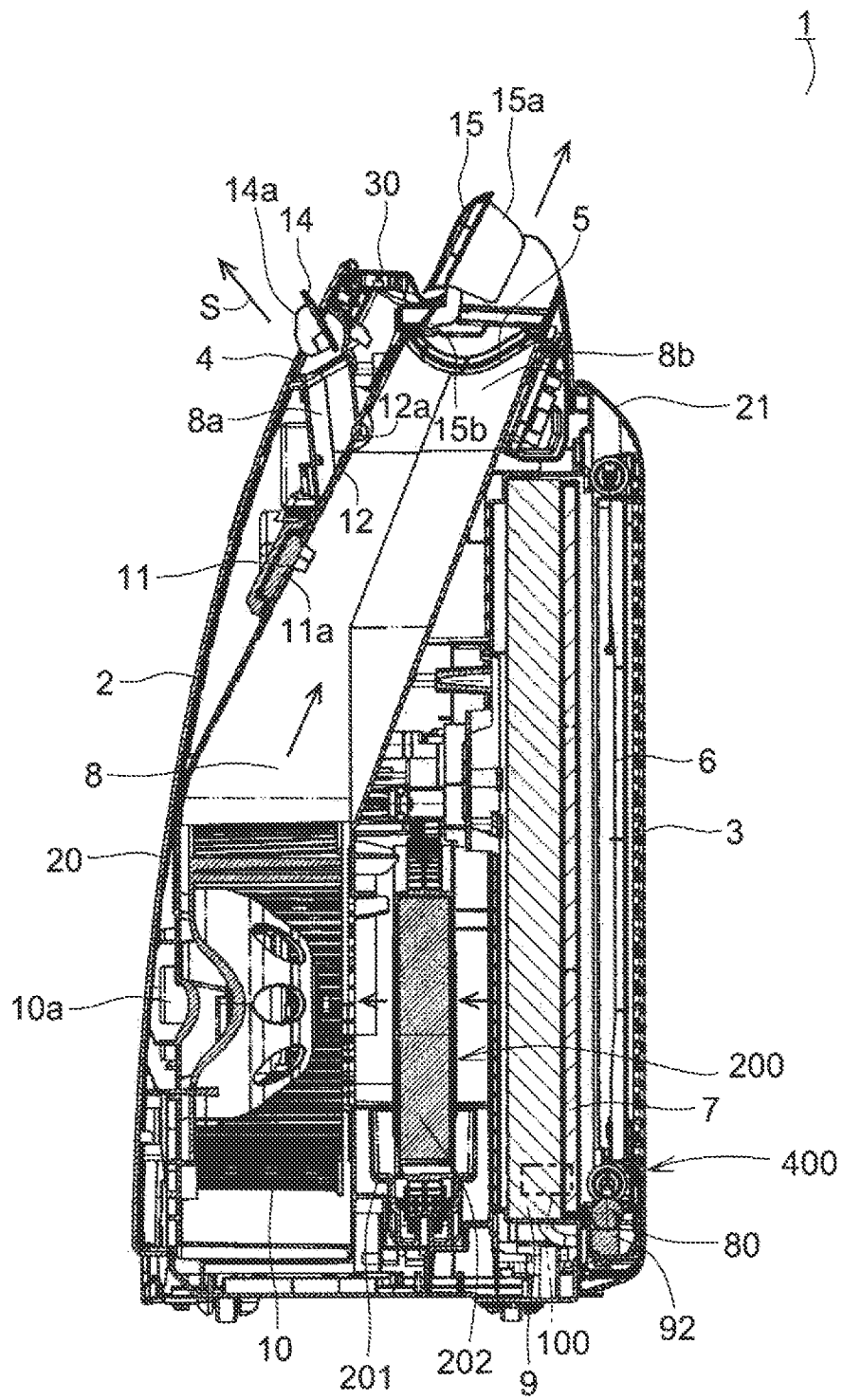
FIG. 2 is a sectional side view illustrating the air purifier of the first embodiment of the disclosure.

An embodiment of the disclosure will be described below with reference to drawings. FIGS. 1 and 2 respectively illustrate a front view and a sectional side view of an air purifier of a first embodiment. Note that, an arrow S indicates a flow of air. An air purifier 1 has a housing 2 in which an inlet 3 and outlets 4 and 5 are opened and which is installed on a floor surface or the like of a living room.

The housing 2 has a main body portion 20 and a cover portion 21. The cover portion 21 is disposed so as to be detachably attachable to a rear surface of the main body portion 20, and opens the inlet 3. In the main body portion 20, the outlets 4 and 5 are opened in an upper part of a front surface and an upper surface, respectively. An operation panel 30 is disposed in a front part of the upper surface.

Air direction plates 14 and 15 that are able to change an air direction are respectively provided in the outlets 4 and 5. The air direction plate 14 is configured by a flat plate and supported by a rotational shaft part (not illustrated), which is provided in the air direction plate 14, so as to be rotatable in an up-and-down direction. In a lower surface of the air direction plate 14, a plurality of vertical louvers 14a are vertically provided so as to be arrayed in a right-and-left direction. The vertical louvers 14a at both side ends are inclined outwardly in the right-and-left direction as being closer to a front side.

The air direction plate 15 is configured by a flat plate and supported by a rotational shaft part 15b, which is provided in a front part of the air direction plate 15, so as to be rotatable in the up-and-down direction. In a lower surface of the air direction plate 15, a plurality of vertical louvers 15a are vertically provided so as to be arrayed in the right-and-left direction. The vertical louvers 15a at both side ends are inclined outwardly in the right-and-left direction as being closer to a back side.

The air direction plates 14 and 15 respectively close the outlets 4 and 5 when the operation of the air purifier 1 is stopped, and respectively open the outlets 4 and 5 during the operation.

An air passage 8 that connects the inlet 3 and the outlets 4 and 5 is provided in an inside of the housing 2. In an inside of the air passage 8, a pre-filter (filter) 6, a deodorizing filter 7, a dust collecting filter 9, a humidifying unit 200, an air blower 10, an ion generator 11, and a damper 12 are provided in order from the inlet 3 to the outlets 4 and 5 (from an upstream side of an air current to a downstream side thereof).

The air passage 8 has a first branch passage 8a and a second branch passage 8b that branch off in the downstream side of the ion generator 11. The first branch passage 8a and the second branch passage 8b are respectively connected to the outlets 4 and 5. A cross section area of an air flow channel of the first branch passage 8a is smaller than a cross section area of an air flow channel of the second branch passage 8b.

The damper 12 is formed into a thin plate shape, and supported by a rotational shaft part 12a so as to be rotatable in the up-and-down direction. The damper 12 is able to rotate from a position at which the first branch passage 8a is closed (refer to FIG. 2) in a direction (counterclockwise direction in FIG. 2) in which the first branch passage 8a is opened. Air volume balance between the first branch passage 8a and the second branch passage 8b is able to be changed by the damper 12.

The air blower 10 is formed by a centrifugal fan, such as a sirocco fan, which is driven by a motor 10a, and sucks air in a shaft direction and discharges air in a circumferential direction.

The pre-filter 6 is formed of a sheet-shaped mesh of polypropylene or the like and disposed in the cover portion 21 so as to face the inlet 3. It is possible to collect large dust in sucked air by the pre-filter 6.

The deodorizing filter 7 is formed into a honeycomb shape, and is able to absorb an odor component in air and deodorize the air.

The dust collecting filter 9 is composed of a HEPA filter, and a frame material (not illustrated) is welded by hot melt so as to cover a filter material (not illustrated). The dust filter 9 is able to collect a minute particle in air, such as fine dust, PM 2.5 a grain size of which is smaller than a predetermined grain size (for example, 3 μm), or pollen.

The humidifying unit 200 has a tray 201, a humidifying filter 202, and a float switch 120. The float switch 120 detects a water level of the tray 201, and, when a fall of the water level is detected, the tray 201 is supplied with water from a tank. The humidifying filter 202 is disposed so as to be movable between a position at which the humidifying filter 202 is immersed in water of the tray 201 and a position at which the humidifying filter 202 is not immersed. When a humidifying operation is turned on, the humidifying filter 202 is immersed in the water of the tray 201, and air that passes through the humidifying filter 202 is humidified. When the humidifying operation is turned off, the humidifying filter 202 is disposed at the position at which the humidifying filter 202 is not immersed in the water of the tray 201, and humidification of the air that passes through the humidifying filter 202 is not performed.

The ion generator 11 has an ion generating surface 11a that generates an ion when a high voltage is applied, and the ion generating surface 11a faces the inside of the air passage 8. A voltage composed of an AC waveform or an impulse waveform is applied to the ion generating surface 11a. In a case where an applied voltage of the ion generating surface 11a is a positive voltage, a positive ion that is mainly composed of $H^+$ $(H_2O)m$ is generated, and, in a case of a negative voltage, a negative ion that is mainly composed of $O_2^-$ $(H_2O)n$ is generated. Here, m and n are integers. $H^+$ $(H_2O)m$ and $O_2^-$ $(H_2O)n$ are flocculated on a surface of a suspended bacteria or an odor component in air and surround the suspended bacteria or the odor component.

Then, as expressed by formulas (1) to (3), [—OH] (hydroxyl radical) or $H_2O_2$ (hydrogen peroxide) each of which is an activated species is flocculated and produced on a surface of a microorganism or the like by a collision, and thereby the suspended bacteria or the like is destroyed. Here, m' and n' are integers. Accordingly, by generating a positive ion or a negative ion and sending the positive ion or the negative ion from the outlet 4 or 5, it is possible to debacterialize and deodorize an inside of a living room.

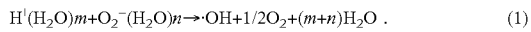

$$H^+(H_2O)m+O_2^-(H_2O)n \rightarrow \cdot OH+1/2O_2+(m+n)H_2O. \quad (1)$$

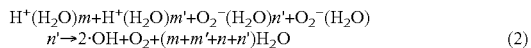

$$H^+(H_2O)m+H^+(H_2O)m'+O_2^-(H_2O)n'+O_2^-(H_2O)n' \rightarrow 2\cdot OH+O_2+(m+m'+n+n')H_2O \quad (2)$$

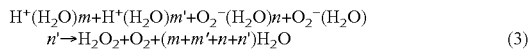

$$H^+(H_2O)m+H^+(H_2O)m'+O_2^-(H_2O)n+O_2^-(H_2O)n' \rightarrow H_2O_2+O_2+(m+m'+n+n')H_2O \quad (3)$$

A cleaning device 400 that cleans the pre-filter 6 is provided in the cover portion 21. The cleaning device 400 moves the pre-filter 6 up and down by drive of a drive motor 100 and removes dust on the pre-filter 6 by a brush body 80. Moreover, the removed dust is collected in a container 92 disposed below the brush body 80.

Figure 3:
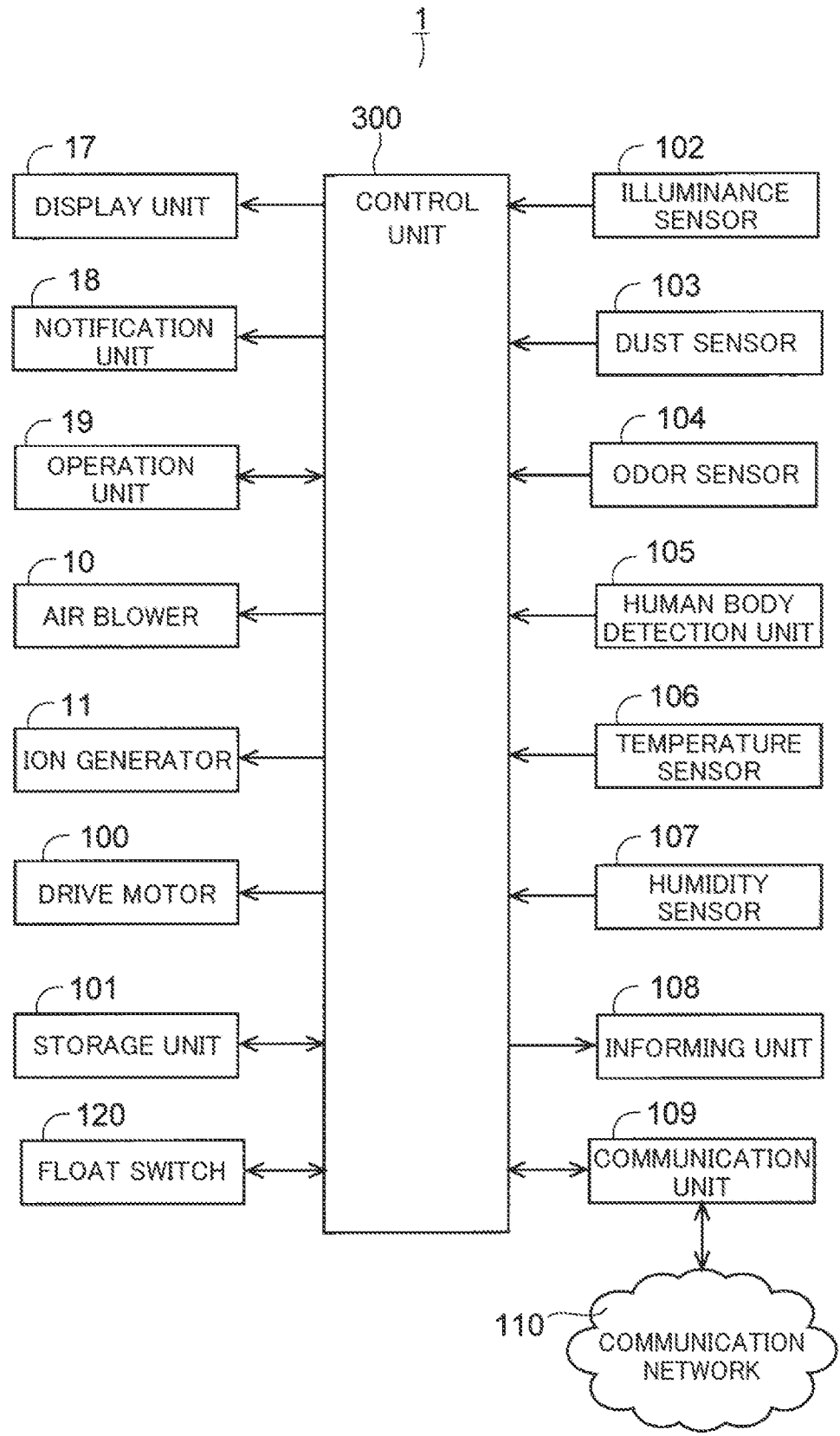
FIG. 3 is a block diagram illustrating the air purifier of the first embodiment of the disclosure.

FIG. 3 is a block diagram illustrating a configuration of the air purifier 1. The air purifier 1 has a control unit 300 that controls each unit and each portion. To the control unit 300, a display unit 17, a notification unit 18, an operation unit 19, the air blower 10, the ion generator 11, the drive motor 100, a storage unit 101, an illuminance sensor 102, a dust sensor 103, an odor sensor 104, a human body detection unit 105, a temperature sensor 106, a humidity sensor 107, an informing unit 108, a communication unit 109, and the float switch 120 are connected.

The control unit 300 reads and executes a control program, which is stored in the storage unit 101 in advance, by a control processor such as a CPU or an MPU. Thereby, drive and stop of the display unit 17, the notification unit 18, the operation unit 19, the air blower 10, the ion generator 11, the drive motor 100, the communication unit 109, and the float switch 120 are able to be controlled.

The storage unit 101 stores the control program of the air purifier 1 and also stores a result of an operation performed by the control unit 300 and a result of detection of the illuminance sensor 102, the dust sensor 103, the odor sensor 104, the human body detection unit 105, the temperature sensor 106, or the humidity sensor 107.

The communication unit 109 performs wireless communication according to a WiFi standard. It is thereby possible to perform an input operation of the air purifier 1 via external equipment such as a personal computer (not illustrated). Moreover, the communication unit 109 is able to download a new control program via a communication network 110 for updating.

The illuminance sensor 102, the temperature sensor 106, and the humidity sensor 107 respectively detect illuminance, temperature, and humidity of an inside of a room where the air purifier 1 is installed.

The dust sensor 103 detects a dust density in air. The odor sensor 104 is disposed near the inlet 3 and detects a density of an odor component (odor density) in the air.

The human body detection unit 105 is constituted by, for example, any of an infrared sensor, an ultrasonic sensor, a visible light sensor, a camera, and the illuminance sensor 102, and detects presence of a person within a predetermined distance range from the air purifier 1. The control unit 300 determines the presence of the person in the room on the basis of an output obtained from the human body detection unit 105.

The informing unit 108 is constituted by a speaker and informs voice guidance.

Figure 4:
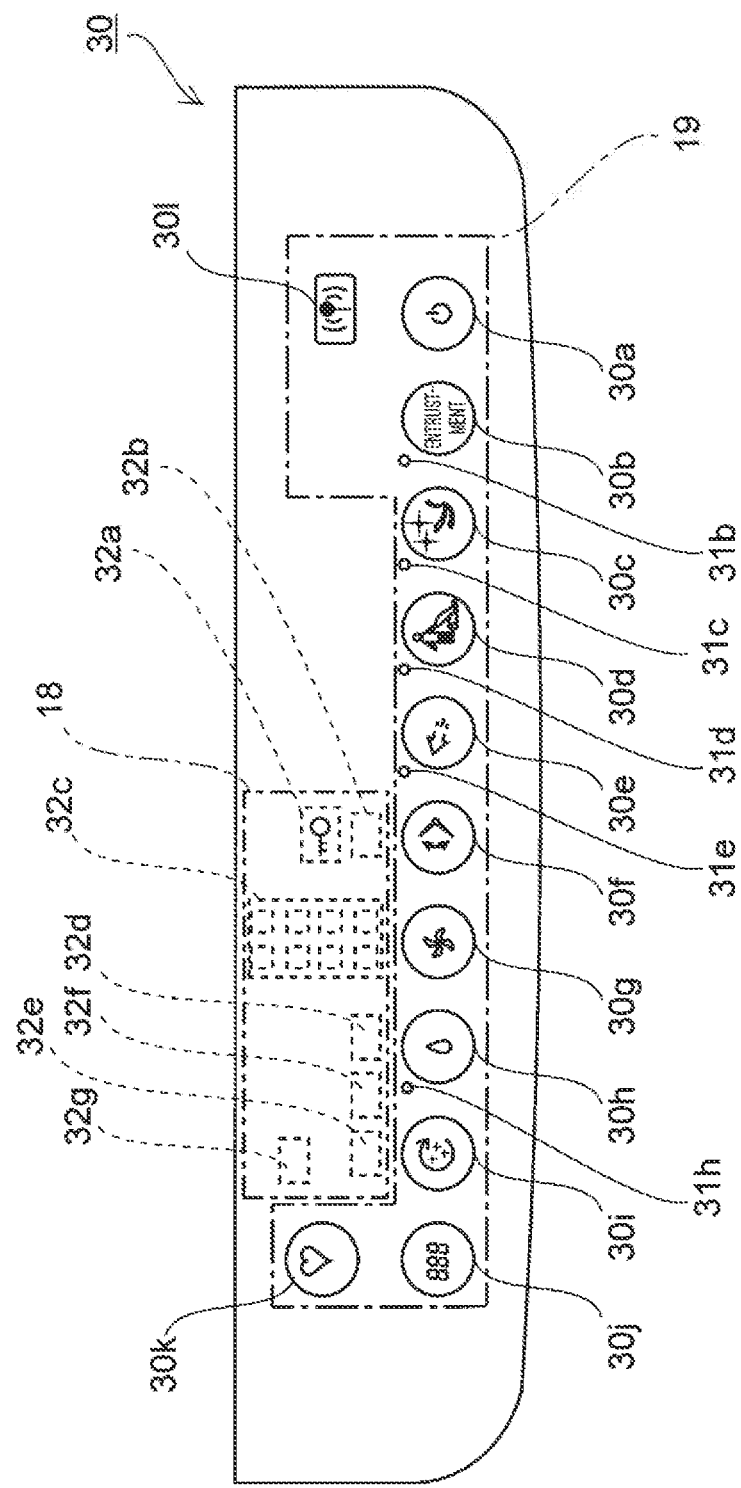
FIG. 4 is a plan view illustrating an operation panel of the air purifier of the first embodiment of the disclosure.

FIG. 4 illustrates a plan view of the operation panel 30. The operation panel 30 includes the notification unit 18 and the operation unit 19.

In the notification unit 18 and the operation unit 19, character display of a so-called light emitting type is performed, except for a touch key 30a, and, when an LED 34 (refer to FIGS. 5 and 6) which is disposed in a rear surface is turned on, a figure (icon) or a series of characters is able to be displayed in an emerging manner. Moreover, by turning off the LED 34, the display on the operation panel 30 is able to be extinguished, so that it is possible to enhance designability.

The notification unit 18 has a plurality of notification regions 32a to 32g. A figure (icon) or a series of characters, which is disposed in each of the regions, is lit up to be displayed and a state of the air purifier 1 is indicated for a user.

The operation unit 19 has a plurality of touch keys 30a to 30l, and operation setting of the air purifier 1 is performed by an operation of the user. The touch key 30a is formed by printing a figure on a front surface panel 35 (FIG. 6) which is described below, and is not lit up to be displayed. On the other hand, in each of the touch keys 30b to 30l, the figure (icon) or the series of characters, which is disposed in a corresponding one of operation regions, is lit up to be displayed for receiving an operation input of the user.

Lamps 31b to 31e and 31h are respectively provided at upper left of the touch keys 30b to 30e and the touch key 30h. By turning on the lamps 31b to 31e and 31h, the user is informed of execution of an operation of the touch keys 30b to 30e and the touch key 30h, respectively.

The touch key 30a is a start key, and an operation and stop of the air purifier 1 are instructed by an operation of the touch key 30a.

By the touch key 30b, a "fully circulating entrustment mode" is executed. On an operation of the touch key 30b, the "fully circulating entrustment mode" is started and the lamp 31b is turned on. In the "fully circulating entrustment mode", a humidifying operation is performed so that humidity becomes 55% to 65%, while automatically adjusting air volume on the basis of results of detection of the dust sensor 103, the odor sensor 104, the temperature sensor 106, and the humidity sensor 107.

By the touch key 30c, an "effect feeling mode" is executed. On an operation of the touch key 30c, the "effect feeling mode" is started and the lamp 31c is turned on. In the "effect feeling mode", during a predetermined time, the air volume is increased and the air direction plates 14 and 15 are rotated backward so as to cause an air current, which blows from the outlet 5, to perform short circuit into the inlet 3. It is thereby possible to concentratedly introduce dust around the air purifier 1 to the inlet 3.

Moreover, in the "effect feeling mode", after a predetermined time elapses from the start of the "effect feeling mode", while driving the ion generator 11, the air direction plates 14 and 15 are rotated forward so that an air current blows forward. It is thereby possible to concentratedly perform deodorization and debacterialization in a front side of the air purifier 1.

By the touch key 30d, a "cleaner assist mode" is executed. On an operation of the touch key 30d, the "cleaner assist mode" is started and the lamp 31d is turned on. In the "cleaner assist mode", during a predetermined time, the air direction plate 14 is rotated forward so that an air current blows forward and downward from the outlet 4, while the outlet 5 is closed by the air direction plate 15. Moreover, while driving the ion generator 11 without humidification, the air volume is increased to a maximum. Thereby, the air current blows toward an installation surface of the air purifier 1, and dust blown up by air discharged from a cleaner is prevented from being attached to the installation surface.

In addition, after a predetermined time elapses from the start of the "cleaner assist mode", the air direction plate 15 is rotated backward so that an air current blows backward and upward from the outlet 5, while the outlet 4 is closed by the air direction plate 14. Thereby, the air current that blows from the outlet 5 is caused to perform short circuit into the inlet 3 to thereby rapidly collect dust which is blown up when the cleaner is used.

By the touch key 30e, a "powerful shot mode" is executed. On an operation of the touch key 30e, the "powerful shot mode" is started and the lamp 31e is turned on. In the "powerful shot mode", while driving the ion generator 11, the air volume is increased. Moreover, the air direction plates 14 and 15 are rotated forward so that air currents that blow from the outlets 4 and 5 are directed forward. It is thereby possible to release positive ions and negative ions in a high concentration concentratedly to a front side of the housing 2 and to eliminate odor and a bacterium that are attached to an object disposed in front of the housing 2.

By the touch keys 30f to 30k, setting as to an air direction, the air volume, and the like is able to be performed when a normal air purifying operation which is different from that of the "fully circulating entrustment mode", the "effect feeling mode", the "cleaner assist mode", or the "powerful shot mode" is executed.

The touch key 30f is a key which is used for both an operation of setting the air direction and an operation of a child lock. By pressing the touch key 30f short, it is possible to fix rotating positions of the air direction plates 14 and 15 at predetermined positions and change directions of air currents that blow from the outlets 4 and 5.

In addition, by pressing the touch key 30f long for three seconds or more, setting or cancellation of the child lock is executed. When the child lock is set, a "key mark" which is disposed in the notification region 32a and characters of "child lock (press for three seconds)" which are disposed in the notification region 32b are lit up and operations on the touch keys 30a to 30k become invalid.

The touch key 30g is used for both an operation of setting the air volume and an operation of setting drive of the ion generator 11. By pressing the touch key 30g short, it is possible to perform eight patterns of setting of the air volume. Moreover, six patterns of characters are disposed in the notification region 32c which is in an upper part of the touch key 30g, and a character disposed in the notification region 32c is lit up in accordance with an air volume setting pattern which is set.

Specifically, the air volume setting patterns are eight patterns of "automatic", "pollen", "sleep", "quiet", "low", "middle", "high", and "turbo", and the air volume setting pattern is changed in order each time the touch key 30g is pressed. When the air volume is set to "automatic", the air volume is automatically set on the basis of results of detection of the illuminance sensor 102, the dust sensor 103, the odor sensor 104, the human body detection unit 105, the temperature sensor 106, and the humidity sensor 107.

Moreover, when the air volume is set to "pollen", sensitivity of the dust sensor 103 is set to be high, and dust or pollen is quickly detected and the pollen or the dust in a room is collected by increasing the air volume compared to that of setting of "automatic".

When the air volume is set to "sleep", the air volume is automatically set on the basis of results of detection of the illuminance sensor 102, the dust sensor 103, the odor sensor 104, the temperature sensor 106, and the humidity sensor 107, and an operation is performed quietly by reducing the air volume compared to that of setting of "automatic".

When the air volume is set to "quiet", "low", "middle", "high", or "turbo", the air volume is increased in order.

In addition, when the touch key 30g is pressed long for three seconds or more, the drive of the ion generator 11 is able to be switched between ON and OFF. When the drive of the ion generator 11 is turned ON, a "plasma cluster ion lamp" (not illustrated) in the display unit 17 is turned on. When the drive of the ion generator 11 is turned OFF, the "plasma cluster ion lamp" (not illustrated) is turned off.

The touch key 30h is an operation key by which care timing notification of the tank (not illustrated), the tray 201, and the humidifying filter 202 of the humidifying unit 200 is set. By an operation of the touch key 30h, setting of the care timing notification of the humidifying unit 200 is turned "ON". Thereby, when an integrated operation time of the air purifying operation exceeds a predetermined time (for example, 720 hours) and an integrated time during which the float switch 120 is in a state of "ON" exceeds a predetermined time (60 minutes), characters of "care for humidifying" disposed in the notification region 32d are lit up. Thereby, the user is informed that care timing of the humidifying unit 200 has come.

Moreover, when the touch key 30h is pressed long for three seconds or more, the characters of "care for humidifying" are extinguished, and the integrated time of the air purifying operation and the integrated time of the time during which the float switch 120 is in the state of "ON" are reset.

The touch key 30i is an operation key by which setting or cancellation of automatic cleaning of the pre-filter 6 is performed. When the automatic cleaning is set by an operation of the touch key 30i, a "pre-filter cleaning lamp" (not illustrated) of the display unit 17 is turned on. Moreover, when the integrated time of the air purifying operation exceeds a predetermined time (for example, 48 hours), the cleaning device 400 is automatically driven and cleans the pre-filter 6.

Further, when the automatic cleaning is cancelled by an operation of the touch key 30i, the "pre-filter cleaning lamp" (not illustrated) of the display unit 17 is turned off. Moreover, when the integrated time of the air purifying operation exceeds a predetermined time (for example, 720 hours), the cleaning device 400 is compulsorily driven and cleans the pre-filter 6.

Note that, when the cleaning device 400 is being driven, the air purifying operation is stopped and the touch key 30i blinks.

In addition, the touch key 30i is also used for a reset operation of disposal timing of dust which is accumulated in the container 92. When the touch key 30i is pressed long for three seconds or more, setting of notification of the disposal timing of dust which is accumulated in the container 92 is reset. Thereby, the integrated time of the air purifying operation exceeds a predetermined time (for example, 4320 hours) after the reset, characters of "garbage disposal" which are disposed in the notification region 32e and characters of "reset (press for three seconds)" which are disposed in the notification region 32f are lit up. Thereby, the user is informed that the disposal timing of dust which is accumulated in the container 92 has come.

Furthermore, when the touch key 30i is pressed long for three seconds or more again, the characters of "garbage disposal" and the characters of "reset (press for three seconds)" are extinguished.

The touch key 30j is an operation key of switching display of the display unit 17. When the touch key 30j is operated, it is possible to display, on the display unit 17, a state of air around the air purifier 1 by switching any of "temperature", "humidity", "density of PM 2.5", and "electric bill".

For "temperature", temperature)(C°) detected by the temperature sensor 106 is displayed. For "humidity, humidity (%) detected by the humidity sensor 107 is displayed. For "density of PM 2.5", density ($\mu g/m^3$) detected by the dust sensor 103 is displayed. For "electric bill", an amount of money (yen) which is calculated from an operation time of the air purifying operation is displayed.

The touch key 30$k$ is an operation key of setting sound volume. By pressing the touch key 30$k$ short, it is possible to change sound volume of the voice guidance that is informed from the informing unit 108. By pressing the touch key 30$k$ long for three seconds or more, it is possible to switch the voice guidance between "ON" and "OFF". When the voice guidance is set to "ON", characters of "sound volume (press for three seconds)" in the notification region 32$g$ are lit up. When the voice guidance is set to "OFF", the characters of "sound volume (press for three seconds)" in the notification region 32$g$ are extinguished.

The touch key 30$l$ is a communication key by which whether or not communication by the communication unit 109 is allowed is instructed. By pressing the touch key 30$l$ long for three seconds or more, it is possible to switch whether or not to allow the communication. Moreover, when the communication unit 109 is in a state where the communication is allowed, a "connect lamp" (not illustrated) in the display unit 17 is turned on. When the communication unit 109 is in a state where the communication is not allowed, the "connect lamp" is turned off.

Figure 5:
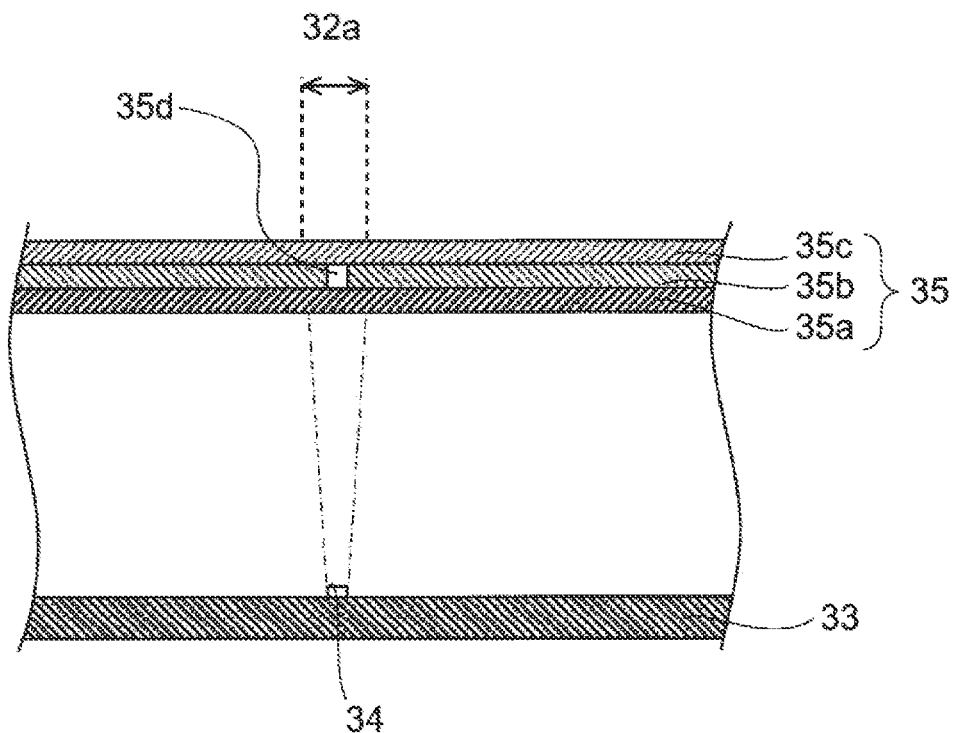
FIG. 5 is a sectional side view illustrating a notification region of the air purifier of the first embodiment of the disclosure.

FIG. 5 is a sectional side view illustrating the notification region of the operation panel. Note that, the notification regions 32$a$ to 32$g$ have similar structures, and description will be given for the notification region 32$a$ as a representative. The notification region 32$a$ includes a substrate 33, the LED 34, and the front surface panel 35. The substrate 33 is a printed wiring substrate and mounted with the LED 34 on an upper surface thereof. Moreover, the front surface panel 35 is disposed above the LED 34.

The front surface panel 35 includes a diffusing member 35$a$, a light shielding member 35$b$, and a light transmitting member 35$c$, and the light shielding member 35$b$ is disposed between the diffusing member 35$a$ and the light transmitting member 35$c$.

The diffusing member 35$a$ diffuses light which is incident and suppresses variation of luminance (luminance unevenness) of light which is transmitted through the front surface panel 35.

The light shielding member 35$b$ is colored in black and shields light emitted from the LED 34. In the light shielding member 35$b$, a slit 35$d$ that forms the figure or the series of characters each of which is disposed in the notification region 32$a$ is opened.

The light transmitting member 35$c$ is disposed in an uppermost surface of the front surface panel 35 and protects the light shielding member 35$b$. The light transmitting member 35$c$ is formed from a material, such as glass, acrylic resin, or polycarbonate resin, which has high transmittance of light. The light transmitting member 35$c$ is composed of a transparent material, and looks black, which is a color of the light shielding member 35$b$, when the front surface panel 35 is viewed from an outside.

When the LED 34 is turned on, light passes through the slit 35$d$ in the notification region 32$a$, but a part other than the slit 35$d$ is shielded from light by the light shielding member 35$b$. Thereby, a figure or a character appears to emerge by the light passing through the slit 35$d$.

On the other hand, when the LED 34 is turned off, no light is transmitted from a lower side of the slit 35$d$ to an upper side thereof, so that it is possible to extinguish display of the notification region 32$a$.

Figure 6:
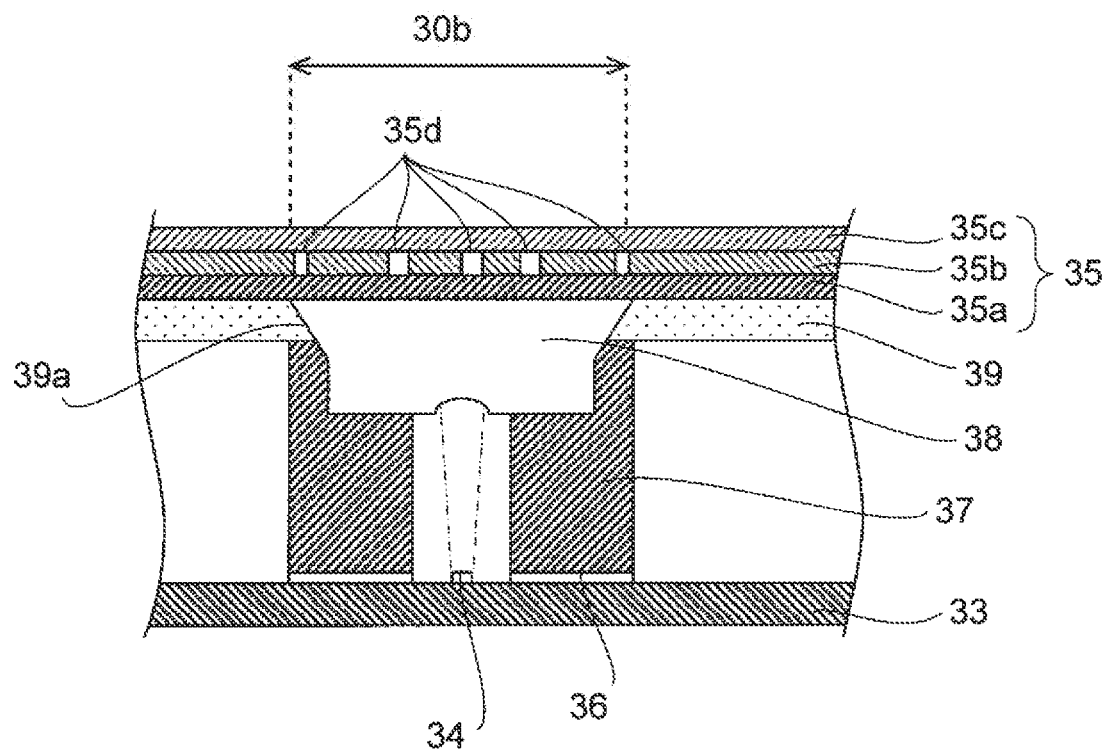
FIG. 6 is a sectional side view illustrating a touch key of the air purifier of the first embodiment of the disclosure.

FIG. 6 is a sectional side view illustrating the touch key of the operation panel. Note that, the touch keys 30$b$ to 30$l$ have the same structure, and description will be given for the touch key 30$b$ as a representative. The touch key 30$b$ includes the substrate 33, the LED 34, the front surface panel 35, an electrostatic sensor 36, a conductive member 37, a lens 38, and a fixing member 39.

Note that, since a configuration of the front surface panel 35 is common with that of the notification region 32$a$, description thereof will be omitted. Also in the touch key 30$b$, when the LED 34 is turned on, a figure or a character appears to emerge by the light passing through the slit 35$d$.

The lens 38 is disposed above the LED 34 and enlarges an irradiation range of light emitted from the LED 34.

The fixing member 39 fixes the lens 38. The fixing member 39 has a through hole 39$a$ that has a cone shape, and holds the lens 38 in such a manner that a lower surface of the lens 38 is in contact with an inclined surface 39$b$ of the through hole 39$a$. Moreover, the fixing member 39 is fixed to the front surface panel 35.

The electrostatic sensor 36 has an annular shape and is mounted on the substrate 33 so as to surround a periphery of the LED. Moreover, the conductive member 37 is disposed between the electrostatic sensor 36 and the lens 38 and between the electrostatic sensor 36 and the fixing member 39.

The electrostatic sensor 36 is a sensor that detects a charge which is accumulated. The electrostatic sensor 36 configures a capacitor by a finger of a user, which touches the front surface panel 35, and the conductive member 37 and detects a charge which is accumulated in the capacitor. That is, the electrostatic sensor 36 detects a change in an electrostatic capacitance which is accumulated in the capacitor and detects contact or separation of the finger of the user with or from the front surface panel 35. When the electrostatic sensor 36 detects contact of the user, the control unit 300 determines that an operation of the touch panel 30$b$ is performed.

Moreover, similarly to the touch key 30$b$, the touch key 30$a$ includes the substrate 33, the front surface panel 35, the electrostatic sensor 36, the conductive member 37, and the fixing member 39, but does not include the LED 34 nor the lens 38. Further, the front surface panel 35 is not provided with the slit 35$d$. A figure (icon) is printed in a lower surface of the light transmitting member 35$c$. In other points, the touch key 30$a$ also has the same configuration as that of the touch key 30$b$.

The touch key 30$a$ is printed to be displayed, and always displayed on the operation panel 30 regardless of whether power of the air purifier 1 is ON or OFF. Therefore, when the power of the air purifier 1 is ON, it is possible to easily start or stop an operation of the air purifier 1, so that convenience is improved.

Figure 7:
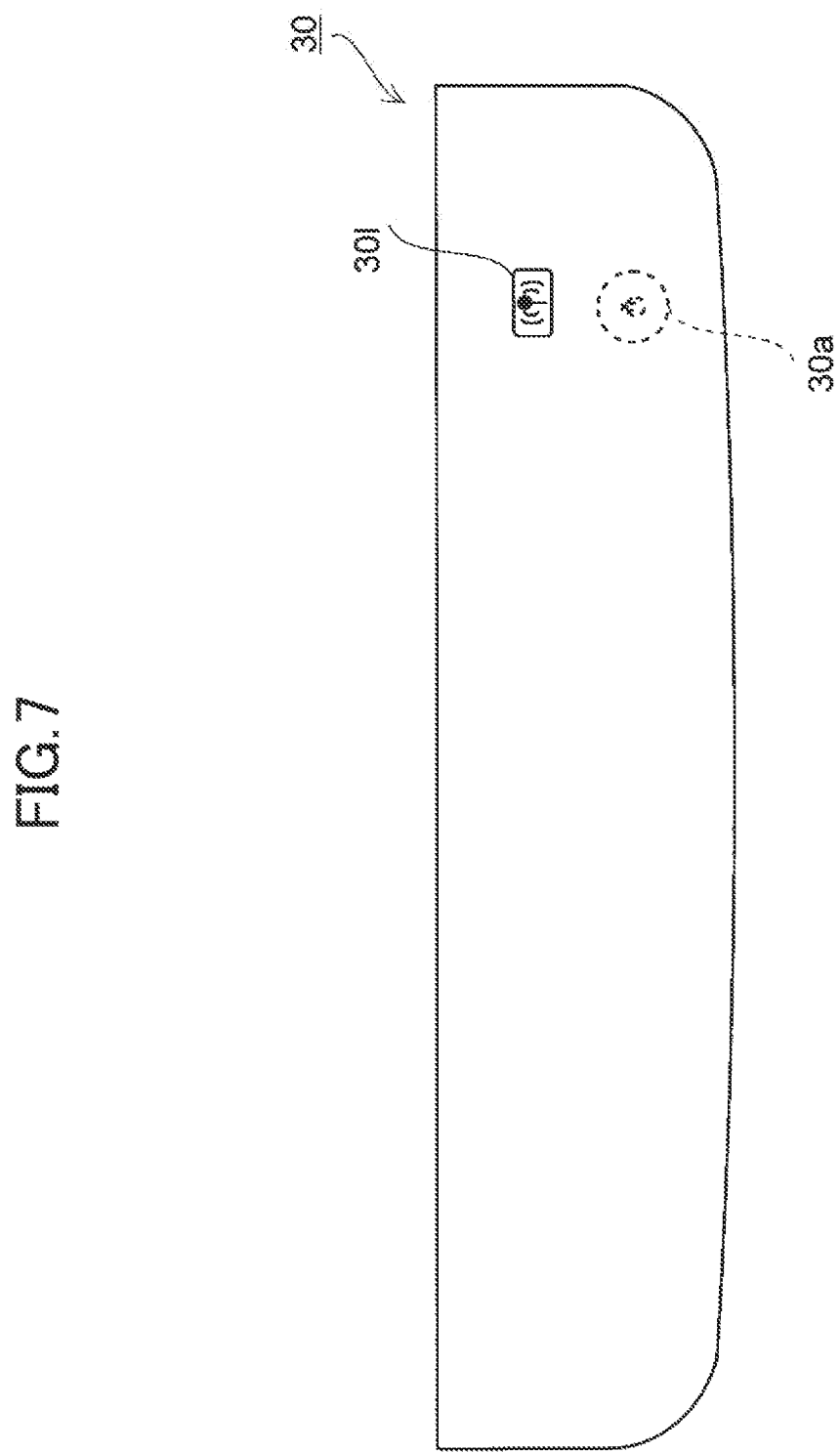
FIG. 7 is a plan view illustrating a display pattern of the operation panel of the air purifier of the first embodiment of the disclosure.

FIG. 7 is a plan view illustrating a display pattern of the operation panel, and illustrates a state where the human body detection unit 105 does not detect presence of a person. The touch key 30$l$ which is lit up to be displayed is indicated by a solid line and the touch key 30$a$ which is printed to be displayed is indicated by a broken line.

When the human body detection unit 105 does not detect presence of a person, the control unit 300 determines that there is no person who operates the operation unit 19 around the air purifier 1. At this time, the control unit 300 turns off all of LEDs 34 of the touch keys 30b to 30k (touch keys of a first group) and the LED 34 (light source for display) of the notification unit 18 and turns on only the LED 34 of the touch key 30l (touch key of a second group).

Thereby, the user is able to recognize the touch key 30l which is lit up to be displayed and the touch key 30a which is printed to be displayed. The user is thus able to easily start or stop the operation of the air purifier 1, so that convenience is improved. Moreover, by turning off the LEDs 34 of the touch keys 30b to 30k of the first group, it is possible to reduce power consumption. In addition, by extinguishing display of the touch keys 30b to 30k from a surface of the operation panel 30, it is possible to enhance designability.

When the human body detection unit 105 detects presence of a person, the control unit 300 determines that there is a person who operates the operation unit 19 around the air purifier 1. At this time, in a case where any of the "fully circulating entrustment mode", the "effect feeling mode", the "cleaner assist mode", and the "powerful shot mode" is executed, the control unit 300 lights up a touch key and a lamp of the executed mode among the touch keys 30b to 30e and the lamps 31b to 31e.

On the other hand, when none of the "fully circulating entrustment mode", the "effect feeling mode", the "cleaner assist mode", and the "powerful shot mode" is executed and a normal air purifying operation is executed, the control unit 300 turns on all of the LEDs 34 of the touch keys 30b to 30k. The user is thereby able to visually and accurately recognize the touch keys 30a to 30k of the operation unit 19 and perform any operation.

Moreover, when the human body detection unit 105 detects presence of a person, the LEDs 34 that correspond to the notification regions 32a to 32g of the notification unit 18 are also turned on. Thereby, when no person is within a predetermined range with respect to the housing 2 of the air purifier 1, it is determined that the notification unit 18 is not seen, and the LEDs 34 of the notification unit 18 are turned off, so that it is possible to further reduce the power consumption.

Moreover, when the user operates a touch key, which is lit up, among the touch keys 30b to 30l, a light amount of the LED 34 is increased. Thus, the user is able to recognize that an operation of the predetermined touch key among the touch keys 30b to 30l is executed, so that convenience is improved.

In addition, each of the touch keys 30f to 30i and the touch key 30k is assigned a function for long press, which is different from that for short press. When any of the touch keys 30f to 30i and the touch key 30k is pressed long for three seconds or more, a corresponding LED 34 blinks. Therefore, the user is able to recognize that a long press operation is executed, so that convenience is improved.

Further, when the touch key 30a is operated and the normal air purifying operation is started, air in a living room is sucked from the inlet 3 and flows in an air passage 8. At this time, large dust in the air is collected by the pre-filter 6. In addition, the air is deodorized by the deodorizing filter 7, and a minute particle in the air, such as fine dust, PM 2.5, or pollen, is collected by the dust collecting filter 9.

Then, an ion generated by the ion generator 11 is contained in the air. The air containing the ion blows into the living room from one or both of the outlets 4 and 5. Thereby, an air sending operation of the air purifier 1 is performed and air purification in the living room is performed.

When predetermined timing has come, the cleaning device 400 is driven and a cleaning operation by the cleaning device 400 is started.

When the cleaning device 400 is driven, the drive motor 100 is rotated, the pre-filter 6 is moved up and down, and the brush body 80 slides on the pre-filter 6. Thereby, dust on the pre-filter 6 is removed and the dust is collected in the container 92.

When a rotation amount of the drive motor 100 reaches a given value, the drive motor 100 is stopped. In the above-described manner, the cleaning operation by the cleaning device 400 ends.

After the cleaning operation by the cleaning device 400 ends, the user is able to remove a dust collecting unit 90 from the cover portion 21 and dispose dust accumulated in the container 92.

According to the present embodiment, in the operation panel 30 including the plurality of touch keys 30b to 30l and the plurality of LEDs 34 (light sources) that respectively correspond to the touch keys 30b to 30l, the human body detection unit 105 that detects presence/absence of a person is provided in the housing 2, and the LEDs 34 of the predetermined touch keys 30b to 30k of the first group are turned off when no person is detected by the human body detection unit 105, and are turned on when a person is detected by the human body detection unit 105. Accordingly, it is possible to reduce power consumption by turning off the LEDs 34 of the touch keys 30b to 30k of the first group when no person is within a predetermined range with respect to the housing 2 of the air purifier 1.

Moreover, the LED 34 of the touch key 30l of the second group which is different from the first group is always turned on, and the touch key 30l is the communication key by which whether or not communication by the communication unit 109 that performs wireless communication is allowed is instructed. Accordingly, since the LED 34 of the touch key 30l is always turned on, even when the air purifying operation is stopped, by operating the touch key 30l, it is possible to easily perform setting as to whether or not to allow the communication, so that convenience is improved.

In addition, when a touch key among the touch keys 30b to 30l, the corresponding LED 34 of which is turned on, is operated, a light amount of the LED 34 is increased, so that the user is able to recognize that the predetermined operation of the touch key among the touch keys 30b to 30l is executed, and convenience is improved.

Further, each of the touch keys 30f to 30i and the touch key 30k is assigned a function for long press, which is different from that for short press. When any of the touch keys 30f to 30i and the touch key 30k is pressed long, a corresponding LED 34 blinks. Therefore, the user is able to recognize that a long press operation is executed, so that convenience is improved.

Furthermore, the operation panel 30 has the notification unit 18 that is displayed when the LED 34 (light source for display) is turned on, and the LED 34 of the notification unit 18 is turned off when no person is detected by the human body detection unit 105, and is turned on when a person is detected by the human body detection unit 105. Accordingly, it is possible to reduce power consumption by turning off the LED 34 of the notification unit 18 when no person is within a predetermined range with respect to the housing 2 of the air purifier 1.

Second Embodiment

Figure 8:
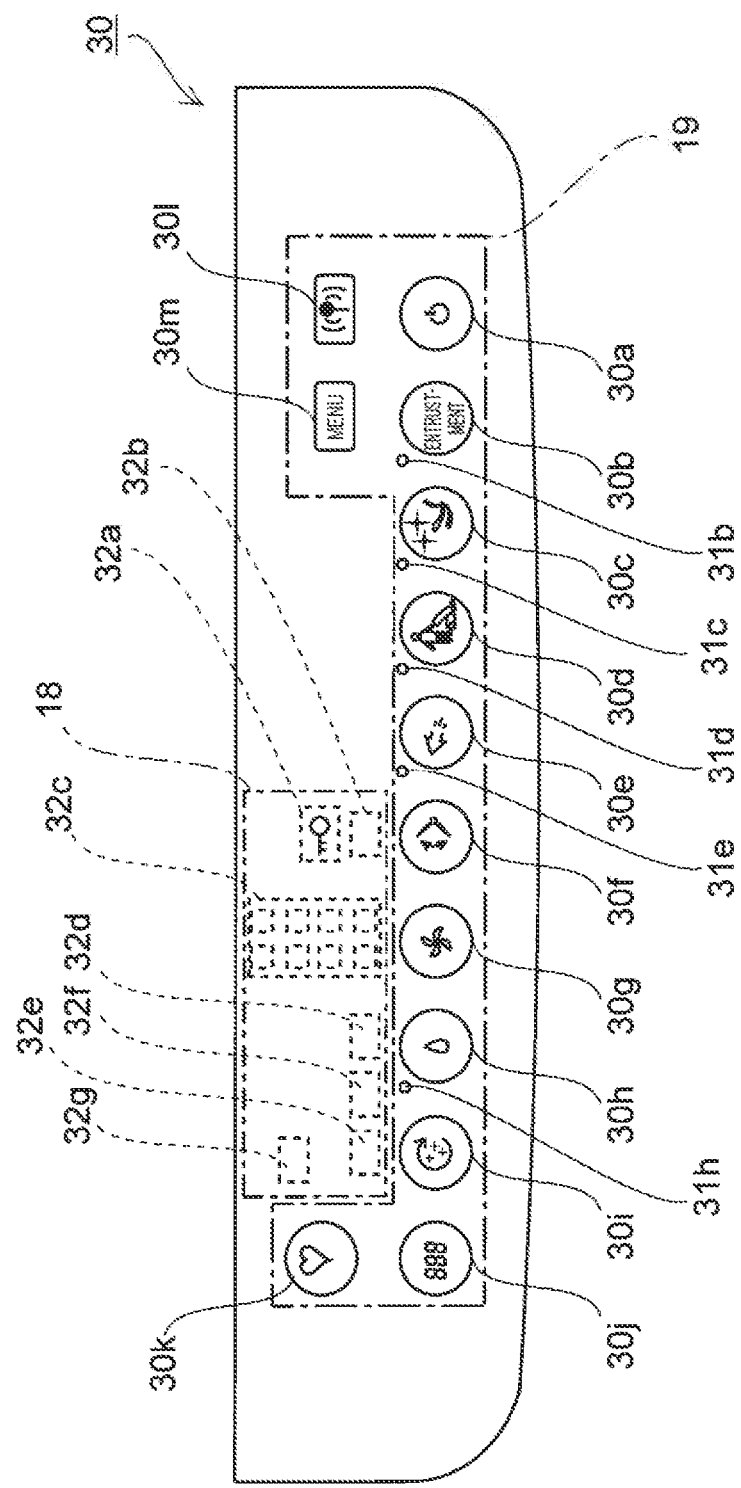
FIG. 8 is a plan view illustrating an operation panel of an air purifier of a second embodiment of the disclosure.

Next, a second embodiment of the disclosure will be described. FIG. 8 is a plan view of an operation panel of an air purifier of the present embodiment. For convenience of description, a part similar to that of the above-described first embodiment which is illustrated in FIGS. 1 to 7 is given the same reference sign. The present embodiment is different from the first embodiment in that the operation unit 19 is provided with a touch key 30m. The other points are similar to those of the first embodiment.

The touch key 30m is an operation key by which menu display is performed. In a case where any of the "fully circulating entrustment mode", the "effect feeling mode", the "cleaner assist mode", and the "powerful shot mode" is executed by an operation of the touch key 30m, a touch key and a lamp of the executed mode among the touch keys 30b to 30e and the lamps 31b to 31e are lit up.

On the other hand, the normal air purifying operation which is different from the "fully circulating entrustment mode", the "effect feeling mode", the "cleaner assist mode", and the "powerful shot mode" is executed, when the user touches the touch key 30m, the control unit 300 turns on the LEDs 34 of all of the touch keys 30b to 30k.

Thereby, the user performs a predetermined operation from the touch keys 30b to 30k which are lit up, and performs operation setting of the air purifier 1. Moreover, when an operation of any of the touch keys 30b to 30k is not performed after a predetermined time (10 seconds) elapses from the operation of the touch key 30m, all of the touch keys 30b to 30k are extinguished.

Figure 9:
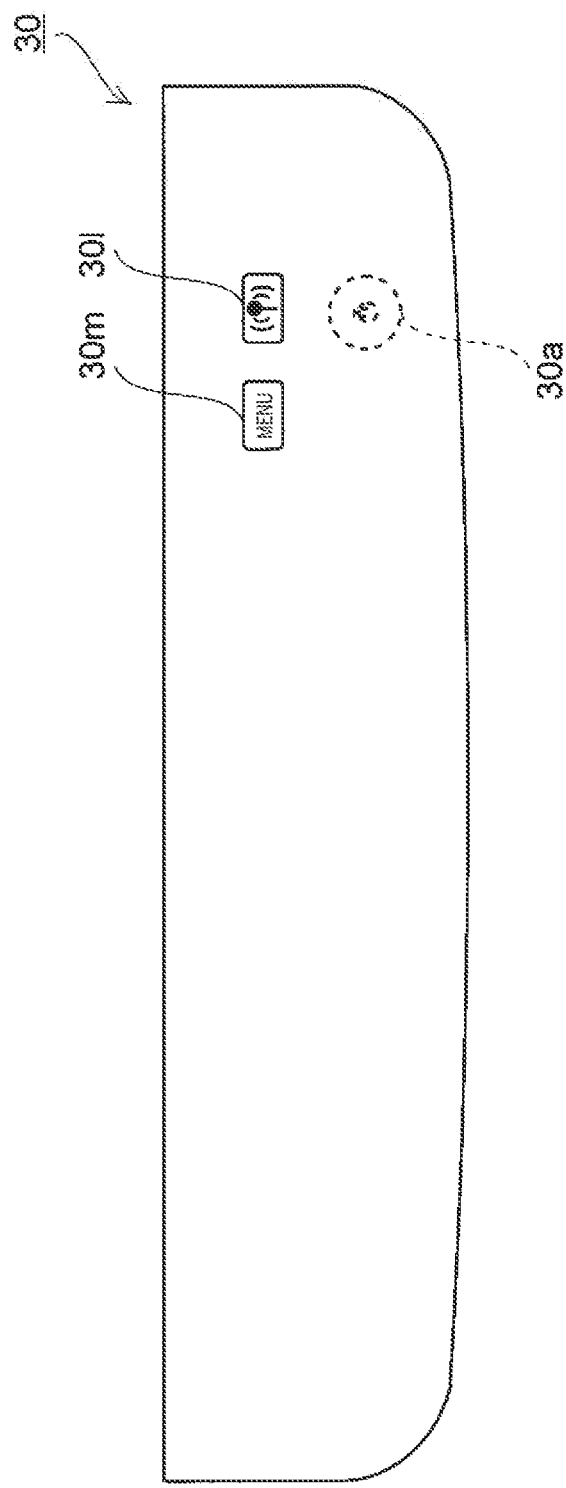
FIG. 9 is a plan view illustrating a display pattern of the operation panel of the air purifier of the second embodiment of the disclosure.

FIG. 9 is a plan view illustrating a display pattern of the operation panel of the air purifier and illustrates a state where the human body detection unit 105 detects presence of a person. Each of the touch keys 30l and 30m which are lit up to be displayed is indicated by a solid line and the touch key 30a which is printed to be displayed is indicated by a broken line.

When the human body detection unit 105 detects presence of a person, the control unit 300 turns on only the LED 34 of the touch key 30m of the first group. Thereby, even when the human body detection unit 105 detects presence of a person, neither the notification unit 18 nor the operation unit 19 is lit up to be displayed as long as the user does not touch the touch key 30m. Thus, it is possible to reduce power consumption by reducing the number of LEDs 34 which are to be turned on when the human body detection unit 105 detects presence of a person.

According to the present embodiment, since the touch keys 30b to 30k of a third group, the LEDs 34 of which are turned on when the touch key 30m of the first group is operated, are included, it is possible to reduce power consumption by reducing the number of LEDs 34 which are to be turned on when the human body detection unit 105 detects presence of a person.

Third Embodiment

Figure 10:
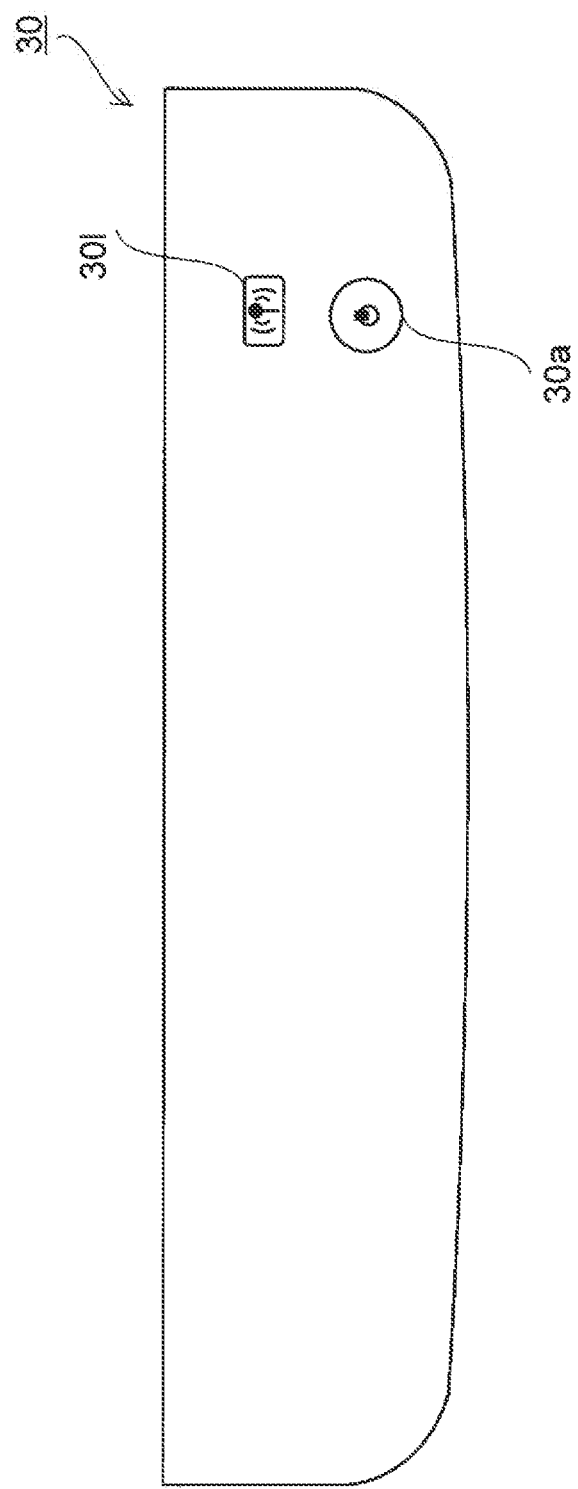
FIG. 10 is a plan view illustrating a display pattern of an operation panel of an air purifier of a third embodiment of the disclosure.

Next, a third embodiment of the disclosure will be described. FIG. 10 is a plan view illustrating a display pattern of an operation panel of an air purifier of the present embodiment and illustrates a state where the human body detection unit does not detect presence of a person. Moreover, each of the touch keys 30a and 30l which are lit up to be displayed is indicated by a solid line. For convenience of description, a part similar to that of the above-described first embodiment which is illustrated in FIGS. 1 to 7 is given the same reference sign. The present embodiment is different from the first embodiment in that the touch key 30a is lit up to be displayed and the touch key 30a is included in the touch keys of the second group. The other points are similar to those of the first embodiment.

The touch key 30a has the LED 34, and, when the LED 34 is turned on, a figure (icon) of the touch key 30a appears to emerge by light passing through the slit 35d. When the human body detection unit 105 does not detect presence of a person, the control unit 300 turns off the LEDs 34 of the touch keys 30b to 30l (touch keys of the first group) of the operation panel 30 and only the touch keys 30a and 30m (touch keys of the second group) are lit up.

Thereby, also in a case where an inside of a room where the air purifier 1 is installed is dark and it is difficult to see printed display, a user is able to accurately grasp a position of the touch key 30a which is always lit up to be displayed. Thus, the user is able to easily start or stop an operation of the air purifier 1, so that convenience is improved.

Note that, lighting display and printed display may be combined for the touch key 30a. Thereby, the user is able to accurately grasp the position of the touch key 30a regardless of brightness of the inside of the room where the air purifier 1 is installed. Thus, it is possible to easily start or stop the operation of the air purifier 1, so that convenience is improved.

Note that, the disclosure is not limited to each of the embodiments described above, and may be modified in various manners, and an embodiment achieved by appropriately combining technical means disclosed in each of different embodiments is also encompassed in the technical scope of the disclosure. For example, not an electrostatic capacitance type but a resistance film type or an electromagnetic induction type may be used for the touch keys 30a to 30m.

Moreover, the touch keys of the first group and the touch keys of the third group do not necessarily include all of the touch keys 30b to 30k, and any of the touch keys 30b to 30k may be selected freely. All of the touch keys of the second group may be printed to be displayed. In this case, the user is able to accurately grasp positions of the touch keys, which are printed to be displayed, similarly to a touch key which is always lit up to be displayed.

In addition, the LEDs 34 (light sources) corresponding to the touch keys of the first group and the touch keys of the third group or the LED 34 (light source for display) of the notification unit 18 may blink when the human body detection unit 105 detects presence of a person.

The LEDs 34 corresponding to the touch keys or the LED 34 of the notification unit 18 is caused to blink, for example, when exchanging timing of the ion generator 11, timing when cleaning of the pre-filter 6 by the cleaning device 400 is required, disposal timing of dust accumulated in the container 92, or care timing of the tray 201 and the humidifying filter 202 is informed, so that it is possible to draw attention of a user more.

Moreover, the light sources of the touch keys of the first group to the third group are not limited to the LEDs 34 that are disposed immediately under the respective touch keys. For example, light sources that are provided around the touch keys of the first group to the third group may be provided as the light sources that correspond to the touch keys. In this case, in a case where the light sources provided around the touch keys are turned on or blink when the human body detection unit 105 detects presence of a person, the user is able to select a predetermined touch key from arrangement of the touch keys, which is grasped in advance, on the basis of the light sources which are turned on or blink and to operate the touch key.

INDUSTRIAL APPLICABILITY

The disclosure is able to be used for an air purifier that includes a touch key for which an input is performed by contact of a finger or the like of a user.

What is claimed is:

1. An air purifier performing an air purifying operation by drive of an air blower, the air purifier comprising: a housing in which an inlet and an outlet are opened; an air passage that connects the inlet and the outlet, the air blower that is disposed in the air passage; a filter that is disposed so as to face the inlet; an operation panel that has a plurality of touch keys and a plurality of light sources which correspond to the respective touch keys; and a communication unit, wherein a human body detection unit that detects presence or absence of a person is provided in the housing, and a light source of a predetermined touch key of a first group is turned off when a person is not detected by the human body detection unit, and is turned on or blinks when a person is detected by the human body detection unit, and wherein the communication unit performs wireless communication, wherein a light source of a touch key of a second group that is different from the first group is always turned on, and the touch key of the second group includes a communication key by which whether or not communication by the communication unit is allowed is instructed.

2. The air purifier according to claim 1, wherein the touch key of the second group includes a start key by which start or stop of the air purifying operation is instructed.

3. An air purifier performing an air purifying operation by drive of an air blower, the air purifier comprising: a housing in which an inlet and an outlet are opened; an air passage that connects the inlet and the outlet, the air blower that is disposed in the air passage; a filter that is disposed so as to face the inlet and an operation panel that has a plurality of touch keys and a plurality of light sources which correspond to the respective touch keys, wherein a human body detection unit that detects presence or absence of a person is provided in the housing, and a light source of a predetermined touch key of a first group is turned off when a person is not detected by the human body detection unit, and is turned on or blinks when a person is detected by the human body detection unit, and wherein a light amount of the light source is increased when the touch key of the light source which is turned on is operated.

4. An air purifier performing an air purifying operation by drive of an air blower, the air purifier comprising: a housing in which an inlet and an outlet are opened; an air passage that connects the inlet and the outlet, the air blower that is disposed in the air passage; a filter that is disposed so as to face the inlet and an operation panel that has a plurality of touch keys and a plurality of light sources which correspond to the respective touch keys, wherein a human body detection unit that detects presence or absence of a person is provided in the housing, and a light source of a predetermined touch key of a first group is turned off when a person is not detected by the human body detection unit, and is turned on or blinks when a person is detected by the human body detection unit, and wherein the predetermined touch key is assigned a function for long press, which is different from that for short press, and the light source is caused to blink at a time of the long press.

5. The air purifier according to claim 1, further comprising:

a touch key of a predetermined group; wherein a light source of the touch key of the predetermined group is turned on when the predetermined touch key of the first group is operated.

6. The air purifier according to claim 1, wherein the operation panel has a notification unit that is displayed when a light source for display is turned on, and the light source for display is turned off when a person is not detected by the human body detection unit, and is turned on or blinks when a person is detected by the human body detection unit.

7. The air purifier according to claim 3, wherein a light source of a touch key of a second group that is different from the first group is always turned on, and the touch key of the second group includes a start key by which start or stop of the air purifying operation is instructed.

8. The air purifier according to claim 3, further comprising: a touch key of a predetermined group; wherein a light source of the touch key of the predetermined group is turned on when the predetermined touch key of the first group is operated.

9. The air purifier according to claim 3, wherein the operation panel has a notification unit that is displayed when a light source for display is turned on, and the light source for display is turned off when a person is not detected by the human body detection unit, and is turned on or blinks when a person is detected by the human body detection unit.

10. The air purifier according to claim 4, wherein a light source of a touch key of a second group that is different from the first group is always turned on, and the touch key of the second group includes a start key by which start or stop of the air purifying operation is instructed.

11. The air purifier according to claim 4, further comprising: a touch key of a predetermined group; wherein a light source of the touch key of the predetermined group is turned on when the predetermined touch key of the first group is operated.

12. The air purifier according to claim 4, wherein the operation panel has a notification unit that is displayed when a light source for display is turned on, and the light source for display is turned off when a person is not detected by the human body detection unit, and is turned on or blinks when a person is detected by the human body detection unit.

* * * * *